US011232604B2

(12) United States Patent
Pan

(10) Patent No.: US 11,232,604 B2
(45) Date of Patent: Jan. 25, 2022

(54) DEVICE FOR MARKING IMAGE DATA

(71) Applicant: EBM TECHNOLOGIES INCORPORATED, Taipei (TW)

(72) Inventor: William Pan, Taipei (TW)

(73) Assignee: EBM TECHNOLOGIES INCORPORATED, Taipei (TW)

( * ) Notice: Subject to any disclaimer, the term of this patent is extended or adjusted under 35 U.S.C. 154(b) by 56 days.

(21) Appl. No.: 16/939,086

(22) Filed: Jul. 27, 2020

(65) Prior Publication Data

US 2021/0350587 A1    Nov. 11, 2021

(30) Foreign Application Priority Data

May 6, 2020  (TW) ................................ 109115022

(51) Int. Cl.
| | | |
|---|---|---|
| *G06T 11/00* | (2006.01) | |
| *G06K 9/32* | (2006.01) | |
| *G06F 3/0482* | (2013.01) | |
| *G06F 3/0484* | (2013.01) | |
| *G16H 30/20* | (2018.01) | |
| *G16H 50/20* | (2018.01) | |
| *G06F 16/11* | (2019.01) | |
| *G06F 16/51* | (2019.01) | |
| *G06N 20/00* | (2019.01) | |
| *G16H 30/40* | (2018.01) | |

(52) U.S. Cl.
CPC ............ *G06T 11/00* (2013.01); *G06F 3/0482* (2013.01); *G06F 3/0484* (2013.01); *G06F 16/116* (2019.01); *G06F 16/51* (2019.01); *G06K 9/3233* (2013.01); *G06N 20/00* (2019.01); *G16H 30/20* (2018.01); *G16H 30/40* (2018.01); *G16H 50/20* (2018.01); *G06T 2200/24* (2013.01); *G06T 2210/41* (2013.01)

(58) Field of Classification Search
CPC ...................................................... G06T 11/00
USPC ........................................................ 715/771
See application file for complete search history.

(56) References Cited

U.S. PATENT DOCUMENTS

| | | | |
|---|---|---|---|
| 6,575,969 B1* | 6/2003 | Rittman, III ....... | A61B 18/1482 606/41 |
| 10,089,752 B1* | 10/2018 | Bronkalla ............ | G06T 7/0012 |
| 2002/0122577 A1* | 9/2002 | Allouche ............... | G06T 7/246 382/131 |
| 2004/0223633 A1* | 11/2004 | Krishnan ............... | G16H 30/20 382/128 |

(Continued)

FOREIGN PATENT DOCUMENTS

| | | |
|---|---|---|
| CN | 106250707 A | 12/2016 |
| TW | 201935590 A | 9/2019 |
| WO | 2017/193251 A1 | 11/2017 |

*Primary Examiner* — Reza Nabi
(74) *Attorney, Agent, or Firm* — Winston Hsu

(57) ABSTRACT

A device including a display panel, a storage circuit, and a processing circuit is provided. The display panel of the device is utilized to display a first image data, and a region of interest can be circled on the first image data. The processing circuit of the device is utilized to receive at least one first mark content and a first region information of the region of interest, and connect the first region information of the region of interest to the at least one first mark content. In this manner, medical professionals can quickly make an initial diagnosis by means of the at least one first mark content of the first image data.

8 Claims, 3 Drawing Sheets

(56) References Cited

U.S. PATENT DOCUMENTS

| | | | | |
|---|---|---|---|---|
| 2005/0054923 | A1* | 3/2005 | Pan | A61B 8/565 600/437 |
| 2005/0069185 | A1* | 3/2005 | Barfuss | G06T 7/73 382/128 |
| 2005/0075556 | A1* | 4/2005 | Pan | A61B 8/00 600/407 |
| 2005/0288568 | A1* | 12/2005 | Pan | G16H 30/20 600/407 |
| 2006/0197913 | A1* | 9/2006 | Pan | H04N 1/0035 352/242 |
| 2006/0282469 | A1* | 12/2006 | Pan | G16H 15/00 |
| 2008/0140722 | A1* | 6/2008 | Jakobovits | G16H 30/40 |
| 2008/0300482 | A1* | 12/2008 | Mlejnek | G06T 19/00 600/425 |
| 2009/0030724 | A1* | 1/2009 | Pan | G06Q 50/20 705/2 |
| 2009/0049104 | A1* | 2/2009 | Pan | G16H 15/00 |
| 2009/0202123 | A1* | 8/2009 | Pan | A61B 8/00 382/128 |
| 2009/0240861 | A1* | 9/2009 | Pan | G09B 7/02 710/267 |
| 2010/0076789 | A1* | 3/2010 | Pan | A61B 8/565 705/3 |
| 2010/0131514 | A1* | 5/2010 | Pan | G16H 30/20 707/741 |
| 2010/0166268 | A1* | 7/2010 | Pan | G16H 30/40 382/128 |
| 2011/0123085 | A1* | 5/2011 | Sebok | G06T 7/73 382/132 |
| 2011/0301980 | A1* | 12/2011 | Martucci | G06Q 10/06 705/3 |
| 2012/0242817 | A1* | 9/2012 | Pan | G06K 9/00134 348/77 |
| 2014/0044325 | A1* | 2/2014 | Ma | G06T 7/33 382/128 |
| 2015/0065812 | A1* | 3/2015 | Pan | G16H 40/67 600/300 |
| 2015/0066523 | A1* | 3/2015 | Pan | A61B 5/0022 705/2 |
| 2015/0139523 | A1* | 5/2015 | Pan | G16H 30/40 382/132 |
| 2016/0000392 | A1* | 1/2016 | Wong Po Foo | A61B 6/481 600/424 |
| 2016/0071264 | A1* | 3/2016 | Agam | G06K 9/3241 382/128 |
| 2016/0210714 | A1* | 7/2016 | Pan | G16H 30/20 |
| 2016/0235868 | A1* | 8/2016 | Meyer | A61K 31/28 |
| 2016/0267068 | A1* | 9/2016 | Nagarajan | G06Q 10/10 |
| 2017/0176239 | A1* | 6/2017 | Pan | G01G 19/44 |
| 2017/0178482 | A1* | 6/2017 | Pan | A61B 5/0205 |
| 2018/0060488 | A1* | 3/2018 | Reicher | G16H 30/20 |
| 2018/0060534 | A1* | 3/2018 | Reicher | G16H 15/00 |
| 2018/0060535 | A1* | 3/2018 | Reicher | G16H 30/40 |
| 2018/0176661 | A1* | 6/2018 | Varndell | G06F 40/197 |
| 2019/0015059 | A1* | 1/2019 | Itu | A61B 6/502 |
| 2019/0076125 | A1* | 3/2019 | Roger | G16H 30/40 |
| 2019/0096060 | A1* | 3/2019 | Zhang | G06T 7/0014 |
| 2019/0122633 | A1* | 4/2019 | Pan | G09G 5/005 |
| 2019/0180488 | A1* | 6/2019 | Hoernig | G06T 7/70 |
| 2019/0188848 | A1* | 6/2019 | Madani | G16H 10/40 |
| 2019/0259494 | A1* | 8/2019 | Sevenster | G16H 30/40 |
| 2019/0333625 | A1* | 10/2019 | Barkan | G16H 30/40 |
| 2020/0054220 | A1* | 2/2020 | Pan | A61B 5/0015 |
| 2020/0054306 | A1* | 2/2020 | Mehanian | G06F 17/18 |
| 2020/0094072 | A1* | 3/2020 | Ritter | A61B 6/5205 |
| 2020/0243183 | A1* | 7/2020 | Goede | G06F 16/5866 |
| 2021/0073977 | A1* | 3/2021 | Carter | G16H 50/20 |
| 2021/0074425 | A1* | 3/2021 | Carter | G16H 50/20 |
| 2021/0248948 | A1* | 8/2021 | Pan | G16H 30/20 |
| 2021/0249117 | A1* | 8/2021 | Pan | G16H 15/00 |

* cited by examiner

DEVICE FOR MARKING IMAGE DATA

BACKGROUND OF THE INVENTION

1. Field of the Invention

The present invention relates to a device for marking image data, and more particularly, to a device for marking image data.

2. Description of the Prior Art

With development of imaging technology of minimally invasive surgery or non-invasive procedure and improvement in image contrast or resolution, importance of image data for medical diagnosis thrives. In order to properly preserve image data, minimize space and reduce costs, digitization of medical information has become a trend. Picture archiving and communication system (PACS) is a computer or network system designed for storage, obtainment, transmission and display of medical images. It stores image data in a digital manner and provides a remote access service to view image data at a distance. However, as the number of image data grows rapidly, it can be time-consuming for medical professionals to review original image data (especially dynamic image data) during each diagnosis. Moreover, interpretation of image data mostly depends on personal skills and experience of medical professionals and is largely down to the individual. Therefore, how to effectively manage, properly label and objectively evaluate image data becomes a worthwhile problem to be solved.

SUMMARY OF THE INVENTION

It is therefore a primary objective of the present invention to provide a device for marking image data, to effectively manage and make use of image data and to promote the progress of medical diagnosis.

An embodiment of the present invention provides a device including a display panel, a storage circuit, and a processing circuit. The display panel of the device is configured to display a first image data. The storage circuit of the device is configured to store the first image data and instructions of receiving at least one first mark content and a first region information of a region of interest, and connecting the first region information of the region of interest to the at least one first mark content. The region of interest is to be selected from the first image data. The processing circuit is coupled to the storage device and configured to execute the instructions stored in the storage circuit.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
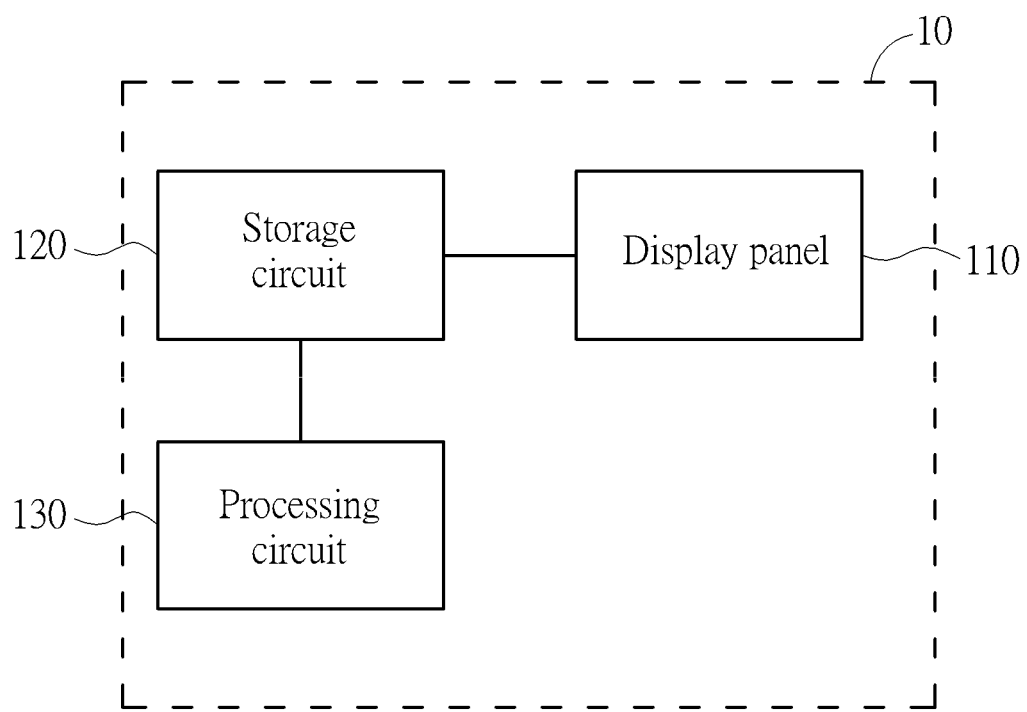
FIG. 1 is a schematic diagram of a device according to an embodiment of the present invention.

FIG. 1 is a schematic diagram of a device 10 according to an embodiment of the present invention. The device 10 may be utilized to process image data such as a first image data. For example, the device 10 may read the image data, mark the image data, or perform artificial intelligence (AI) image recognition. The device 10 includes a display panel 110, a processing circuit 130, and a storage circuit 120. The display panel 110 is configured to display the image data. The storage circuit 120 is configured to store the image data or instructions. The storage circuit 120 may be a subscriber identity module (SIM), read-only memory (ROM), flash memory, random access memory (RAM), disc read-only memory (CD-ROM/DVD-ROM/BD-ROM), magnetic tape, hard disk, optical data storage device, non-volatile storage device, non-transitory computer-readable medium, but is not limited thereto. The processing circuit 130 may be a central processing unit (CPU), a microprocessor, or an application-specific integrated circuit (ASIC), but is not limited thereto.

In short, by tagging the image data, medical professionals would be able to understand medical condition quickly and efficiently by means of mark content(s) of the image data in every medical diagnosis without reexamining the original image data. Medical professionals would be able to comprehend diagnosis results of other medical professionals through the mark content(s) of the image data, thereby enhancing reliability of medical diagnosis or allowing other diagnosis conclusions different from but based on the diagnosis results. The mark content(s) of the image data may form the basis of learning to a freshman and facilitate medical data management. Therefore, the device 10 is conducive to medical quality.

Figure 2:
FIG. 2 is a schematic diagram of a user interface provided by the device shown in FIG. 1 according to an embodiment of the present invention.

Specifically, the device 10 may be configured to execute an application program so as to provide a user interface (UI) to a user. The user interface may be a graphical user interface (GUI). For example, FIG. 2 is a schematic diagram of a user interface 20 provided by the device 10 shown in FIG. 1 according to an embodiment of the present invention. The user interface 20 may include an image window 210, information fields 221, 223, timing bars 225, 245, operation icon buttons 228, 238, 246, 248, edit icon buttons 252, 254, 256, 258, and mark content fields 261 to 267.

The image window 210 may be configured to display the first image data. The first image data may be dynamic image data (such as a video) or static image data (such as a photo). The dynamic image data (for example, the first image data) may include a plurality of static frames, and each frame includes a plurality of pixels arranged in an array. The static image data (for example, the first image data) may include a plurality of pixels arranged in an array. The first image data may be audio video interleave (AVI), windows media video (WMV), real media variable bitrate (RMVB), moving pictures experts group (MPG), MOV, MP4, M4V, 3GP, MKV, RM, XVID or other file formats. Alternatively, the first image data may be digital imaging and communications in medicine (DICOM), bitmap (BMP) or other file formats, but not limited thereto. The first image data may be taken by gastrointestinal endoscopy; however, the first image data may be obtained from other medical imaging techniques with medical imaging equipment(s) such as ultrasound image, magnetic resonance imaging (MRI), positron tomography (PT), computed tomography (CT), mammography (MG), digital radiography (DR), computed radiography (CR), and X-ray plain film (PF).

In FIG. 2, the information field 221 may be configured to present a time point of the first image data currently being played. The information field 223 may be configured to present a total length (namely, length of time) of the first image data. The timing bar 225 may be configured for a user to adjust a time point to play the first image data by scrolling the timing bar 225. The operation icon button 228 may include operation options such as "playback" or "pause". The operation icon button 238 may include operation options such as "stop", "zoom", "rotate", "mirror flip", or "capture a screen". The timing bar 245 may be configured for the user to fine-tune a time point to play the first image data. The operation icon button 246 may include, for example, functions of viewing the previous screen, and the operation icon button 248 may include, for example, functions of viewing the next screen.

As described above, the user may mark the first image data displayed in the image window 210. For example, after the first image data is imported into an application program, the image window 210 may render the first image data for the user to browse. When the application program plays or presents the first image data, the user may pause the first image data by accessing the operation icon button 228 and then label the first image data. In addition, the user may fine-tune with the timing bar 245 or by clicking on the operation icon buttons 246 and 248 to find a frame to be marked. When the user finds the frame to be marked, the user may select a region of interest (ROI) R2 on the first image data by dragging a cursor or touch sensing solutions so as to initiate labeling. Alternatively, the user may select the region of interest R2 on the first image data with lasso tool of a specific pattern so as to initiate labeling. In some embodiments, the user may measure a size of the region of interest R2.

Figure 3:
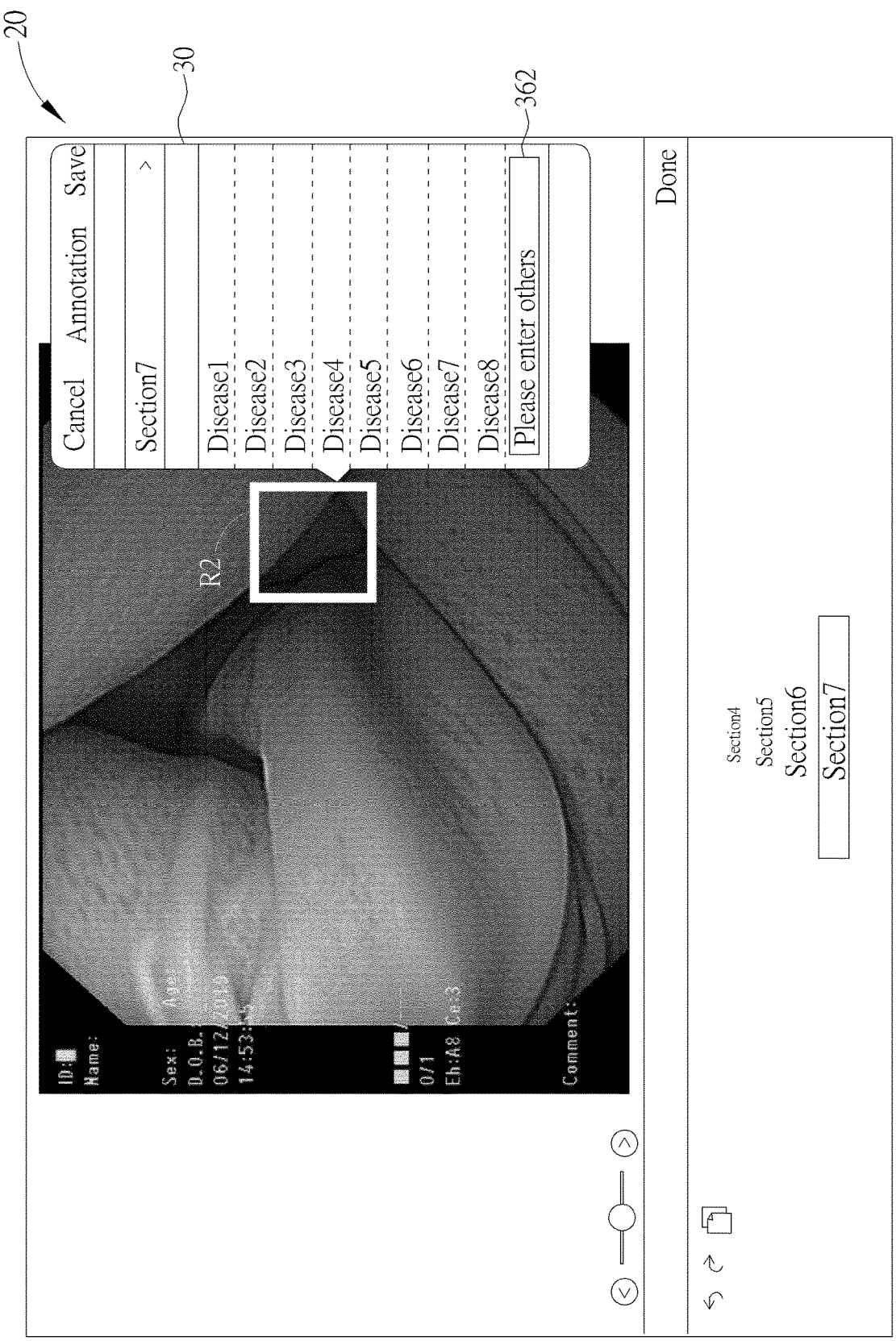
FIG. 3 is a schematic diagram of the user interface of the device and a mark option window according to an embodiment of the present invention.

In some embodiments, after the region of interest R2 is circled on the first image data, the application program automatically presents a mark option window. For example, FIG. 3 is a schematic diagram of the user interface 20 of the device 10 shown in FIG. 1 and a mark option window 30 according to an embodiment of the present invention. The mark option window 30 may be configured to present categories Section4-Section7 and options Disease1-Disease8. The user may check off the option Disease7 in the category Section7 in the mark option window 30, such that the option Disease7 is input as a first mark content so as to mark and detail type of suspected disease(s). Similarly, the user may select certain option(s) from the category Section6 in the mark option window 30, such that other information is input as the first mark content so as to mark and detail a tumor as a benign or malignant tumor. The categories or options in the mark option window 30 may be set by the user after the first image data is imported into the application program. For example, the application program may request the user to set the categories Section4 to Section7 or the options Disease1 to Disease8 to be presented in the mark option window 30. Alternatively, the categories or options in the mark option window 30 may be preset in the application program as default. After the user finishes labeling the first image data, the categories or options selected by the user in the mark option window 30 may be presented in the mark content fields 261-267 and may be arranged in order of characteristics according to the categories or options. In this manner, the user may directly mark content(s) (for example, to serve as the first mark content) of preliminary diagnosis (or initial diagnosis) on the first image data, thereby improving quality of medical diagnosis.

In some embodiments, the user may directly key in text content (s) to be annotated (for instance, the first mark content) into a text input field 362 in the mark option window 30 according to its category (for instance, the category Section7). The first mark content may include at least one of atypical cell tissue(s), suspected wound(s), suspected disease(s), suspected tumor(s), suspected benign tumor(s) and suspected malignant tumor(s). In other embodiments, after the region of interest R2 is circled on the first image data, the application program automatically presents a text input window. The user may directly key in the text content(s) to be annotated (for instance, the first mark content) into the text input window. The first mark content may include at least one of atypical cell tissue(s), suspected wound(s), suspected disease(s), suspected tumor(s), suspected benign tumor(s) and suspected malignant tumor(s). For example, the user may type information such as whether there is a tumor in a text input field of the text input window and enter information such as type of suspected disease(s) in another text input field of the text input window. After the user finishes marking the first image data, the text content(s) (namely, the first mark content) entered by the user in the text input window may be presented in the mark content fields 261-267. That is to say, the user may directly key in content(s) of preliminary diagnosis on the first image data, thereby improve quality of medical diagnosis.

After the user finishes annotating the first image data, the user may discard the mark(s) (for instance, the first mark content or the specific pattern enclosing the region of interest R2). For example, the user may click an option Cancel on the mark option window 30 shown in FIG. 3. Alternatively, the user may press the edit icon buttons 252-258 shown in FIG. 2. The edit icon button 252 may be configured to trigger a restoration action, which involves, for instance, undoing an action or returning to the previous step. The edit icon button 254 may be configured to trigger a cancellation of the restoration action, which involves, for instance, redoing an action, which has been undone, or turning to the next step. The edit icon button 256 may be configured to trigger a mark modification action like an eraser. The edit icon button 258 may be configured to trigger a clear action, for example, to clear the entire screen.

After the user finishes annotating the first image data, the user may save the mark(s) (for instance, the first mark content or the specific pattern enclosing the region of interest R2). For example, the user may press the option Save on the mark option window 30. Correspondingly, the device 10 would store the first mark content and a first region information of the region of interest R2. The first region information of the region of interest R2 may be associated with position of the region of interest R2. For example, the device 10 may store position information of first pixel(s). In some embodiments, the first pixel may be a pixel located at a geometric center of the region of interest R2. In other embodiments, the first pixels may locate around an edge of the region of interest R2 and surround the region of interest R2. Alternatively, the first pixels may distribute separately and be scattered along the edge(s) of the region of interest R2. In other embodiments, it is possible to locate the region of interest R2 by means of the first pixel(s). For example, a rough location or contour of the region of interest R2 may be determined or depicted with the first pixel(s). In other embodiments, the first pixels may be arranged in a specific shape such as a circle, a rectangle, a triangle, or a combination thereof. In other words, the device 10 may store the first mark content and the first region information of the first image data corresponding to the first mark content.

Subsequently, the device 10 may link the first region information of the region of interest R2 and the first mark content. For example, the device 10 may store the first region information of the region of interest R2 and the first mark content in a JavaScript Object Notation (JSON) file format or other JavaScript file format, but not limited thereto. Alternatively, the first mark content of the first image data may also be saved in plain text format. In some embodiments, the user may export the first image data with the mark (s) (for instance, the first mark content or the specific pattern enclosing the region of interest R2) by email or by uploading to the network.

It may require that gray level (also referred to as gray scale) or color distribution of the first image data meets specific requirements so as to improve accuracy of medical diagnosis and facilitate artificial intelligence image recognition. In some embodiments, the operation icon button 238 shown in FIG. 2 may further include operation options such as automatic recognition of ambient light source or display of gray level correction in order to ensure that the first image data displayed by the device 10 meet a gray level curve. It may thus prevent medical professionals from making wrong judgments and ensure interpretation accuracy of the first image data. For example, the first image data presented in the image window 210 has sufficient distinguishable differences to facilitate medical diagnosis by medical professionals. In other embodiments, the device 10 may perform gray level correction on the first image data when importing the first image data or exporting the first image data with the mark(s), such that the first image data conforms to the gray level curve.

The first image data with the mark(s) may not only be utilized by medical professionals to conduct consultations but also be adopted as training data for artificial intelligence image recognition. Artificial intelligence image recognition may infer a second mark content (including, for example, type of suspected disease) or a second region information (including, for example, position where the disease occurs) from a second image data, which is the unknown. Artificial intelligence image recognition may include deep learning, (linear or nonlinear) regression algorithm, Bayesian network and other techniques, but not limited thereto.

In deep learning technology, neural networks can be trained to achieve optimization by means of large amounts of data and automatic training and automatically perform feature extraction, thereby advantageous to complex tasks or data processing. The neural network may include a plurality of neural network layers, and each neural network layer may include a plurality of neurons. For example, the neural network may include a convolutional neural network (CNN), a recurrent neural network (RNN), a feedforward neural network (FNN), a long short-term memory (LSTM) network, a gated recurrent unit (GRU), an attention mechanism, a fully-connected layer or a pooling layer.

Specifically, in order to establish an artificial intelligence model, it is necessary to determine and configure type of each neural network layer, number of the neural network layers, connection method of the neural network layers, number of neurons per layer (namely, per neural network layer), number of parameters, initial values (or default values) of the parameters or activation function(s) in the very beginning. In a training stage of artificial intelligence image recognition, it is required to input a plurality of image data to the artificial intelligence model. The image data may include medical image data with suspected malignant tumor (s), suspected benign tumor(s), suspected inflamed tissue(s), diagnosed malignant tumor(s), diagnosed benign tumor(s), or diagnosed inflamed tissue(s), and, for example, include the first image data. The region(s) of interest (for example, the region of interest R2) marked in the image data (for example, the first image data) may have a specific gray level distribution, color distribution, three-dimensional height distribution, or smoothness, but not limited thereto. With the image data, the parameters of the artificial intelligence model may be trained and optimized. For example, using forward propagation, output of the neural network may be calculated from the first image data according to different parameters. There is a total error between the output of the neural network and a target. All the parameters may be updated recursively using back propagation, such that the output of the neural network gradually approaches the target to minimize the total error. The parameters may thus be optimized to complete the training stage. In other words, the parameters of the artificial intelligence model may be trained by means of the first image data, the first region information, and the first mark content.

In an inference stage of artificial intelligence image recognition, the artificial intelligence model may perform inference on the second image data to be recognized according to the optimized parameters so as to generate an image recognition output associated with screening result(s). The image recognition output may include at least one second region information or at least one second mark content. Each second region information corresponds to (or is related to) one second mark content. The second mark content of the second image data corresponds to (or is similar to) the first mark content of the first image data. The second mark content may include at least one of atypical cell tissue(s), suspected wound(s), suspected disease type(s), suspected tumor(s), suspected benign tumor(s) and suspected malignant tumor(s). The second region information of the second image data corresponds to (or is similar to) the first region information of the first image data. The second region information may be related to position(s) of atypical cell tissue(s), suspected wound(s), suspected disease(s), suspected benign tumor(s) and suspected malignant tumor(s). In some embodiments, the second image data may be marked with the second region information or the second mark content. For instance, a region with a suspected tumor may be circled on the second image data, and text content about the suspected tumor may be presented nearby. The region marked on the second image data (for instance, a specific pattern being circled) may have a specific gray level distribution, color distribution, three-dimensional height distribution, or smoothness, but not limited thereto. In other words, the artificial intelligence model may perform inference on the second image data, and output the second region information or the second mark content to conduct a preliminary diagnosis so as to help medical professionals interpret the medical image data, thereby improving quality of medical diagnosis.

In order to improve accuracy of artificial intelligence image recognition, in some embodiments, image processing is performed on the plurality of image data (such as the first image data) before the image data is input into the artificial intelligence model. In some embodiments, before the first image data is input into the artificial intelligence model, the first image data may be converted into a specific format such as the joint photographic experts group (JPG) format and a portable network graphics (PNG) format. In some embodiments, before the first image data is input into the artificial intelligence model, the first image data may be compensated by means of less-noise (or noise-free) approaches or less-distortion (or undistorted) approaches. For example, the first image data may be calibrated by histogram equalization. In some embodiments, before the first image data is input into the artificial intelligence model, filtering processing may be performed to reduce or get rid of noise in the first image data or improve smoothness. In some embodiments, before the first image data is input into the artificial intelligence model, gray level correction may be implemented so that the first image data conforms to the gray level curve. In some embodiments, before the first image data is input into the artificial intelligence model, the first image data may be normalized according to an average intensity of the first image data in spatial domain, time domain, or frequency domain.

In some embodiments, the device 10 may be a mobile device or other electronic device such as a mobile phone, tablet, personal computer, and medical equipment. In this way, doctor(s) may view images remotely and make remote medical diagnosis. Besides, technology of medical display devices may be integrated into electronic devices with sufficient hardware specifications, thereby increasing popularity and mobility of medical image display. In some embodiments, the storage circuit 120 of the device 10 may be utilized to store the first image data, the second image data, the artificial intelligence model, and its parameters. In some embodiments, the application program of the device 10 may execute the artificial intelligence model according to the second image data and the parameters of the artificial intelligence model to generate the image recognition output related to screening result(s). In this way, the application program of the device 10 may complete a preliminary diagnosis and provide position(s) of suspected tumor(s) to medical professionals for medical diagnosis, which could improve quality of medical diagnosis.

In summary, the device of the present invention may label the first image data; therefore, medical professionals are able to understand medical condition quickly and efficiently by means of the first mark content of the first image data in every medical diagnosis instead of reexamining the original first image data, which can improve medical quality. The first image data with the mark(s) may be utilized as training data for artificial intelligence image recognition. The artificial intelligence model trained with the first image data may be used for artificial intelligence image recognition, and suspected tumor tissue(s) or atypical cell tissue(s) may be identified from the second image data for medical professionals to analyze.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A device, comprising:
a display panel, configured to display a first image data;
a storage circuit, configured to store the first image data and instructions of:
receiving at least one first mark content and a first region information of a region of interest, wherein the region of interest is to be selected from the first image data; and
connecting the first region information of the region of interest to the at least one first mark content; and a processing circuit, coupled to the storage device, configured to execute the instructions stored in the storage circuit, wherein the instruction further includes:
automatically presenting a mark option window on the display panel after the region of interest is selected from the first image data, wherein the text input window is configured to input the at least one first mark content, and the mark option window is configured to present a plurality of options including the at least one first mark content,
wherein parameters of an artificial intelligence model are trained according to the first image data, the first region information, and the at least one first mark content, the artificial intelligence model generates an image recognition output when a second image data is input to the artificial intelligence model having been trained, the image recognition output includes at least one second region information or at least one second mark content.

2. The device of claim 1, wherein the step of receiving the first region information of the region of interest includes: storing a position information of at least one first pixel, wherein the at least one first pixel is located around an edge of the region of interest or at a geometric center of the region of interest.

3. The device of claim 2, wherein: the first image data is dynamic image data, the first image data includes a plurality of static frames, each of the plurality of static frames includes a plurality of pixels arranged in an array, and the plurality of pixels includes the at least one first pixel; or
the first image data is static image data, the first image data includes a plurality of pixels arranged in an array, and the plurality of pixels includes the at least one first pixel.

4. The device of claim 1, wherein the at least one first pixel encloses the region of interest, or wherein the region of interest is locatable according to the at least one first pixel.

5. The device of claim 1, wherein the at least one first mark content includes at least one of an atypical cell tissue, suspected wound, suspected disease, suspected tumor, suspected benign tumor, and suspected malignant tumor.

6. The device of claim 1, wherein the step of connecting the first region information of the region of interest to the at least one first mark content comprises: storing the first region information of the region of interest and the at least one first mark content in a JavaScript Object Notation file format.

7. The device of claim 1, wherein the instruction further includes:
importing the first image data; and requesting to set the plurality of options to be presented in the mark option window after the first image data is imported.

8. The device of claim 1, wherein an image processing is performed on the first image data before the first image data is input to the artificial intelligence model.

* * * * *